(12) United States Patent
St. Germain

(10) Patent No.: US 9,986,736 B2
(45) Date of Patent: Jun. 5, 2018

(54) HERBICIDE COMPOSITIONS AND METHODS FOR CONTROLLING GROWTH OF PLANTS OF THE BUCKTHORN FAMILY

(71) Applicant: Timothy St. Germain, Guelph (CA)

(72) Inventor: Timothy St. Germain, Guelph (CA)

( * ) Notice: Subject to any disclaimer, the term of this patent is extended or adjusted under 35 U.S.C. 154(b) by 0 days. days.

(21) Appl. No.: 15/455,216

(22) Filed: Mar. 10, 2017

(65) Prior Publication Data

US 2017/0258083 A1    Sep. 14, 2017

Related U.S. Application Data

(60) Provisional application No. 62/307,379, filed on Mar. 11, 2016.

(30) Foreign Application Priority Data

Mar. 14, 2016   (CA) ...................................... 2923767

(51) Int. Cl.
*A01N 35/06* (2006.01)

(52) U.S. Cl.
CPC .................................. *A01N 35/06* (2013.01)

(58) Field of Classification Search
None
See application file for complete search history.

(56) References Cited

U.S. PATENT DOCUMENTS

| | | | |
|---|---|---|---|
| 6,106,854 A | 8/2000 | Belfer et al. | |
| 6,164,244 A * | 12/2000 | Cutler ................... | A01K 61/00 119/215 |
| 9,149,825 B1 | 10/2015 | Blakeslee et al. | |
| 2004/0039353 A1 | 2/2004 | Koenig et al. | |
| 2004/0185123 A1 | 9/2004 | Mazzio et al. | |
| 2011/0053773 A1 | 3/2011 | Armel et al. | |

FOREIGN PATENT DOCUMENTS

| | | |
|---|---|---|
| CA | 1179269 | 12/1984 |
| CA | 2928061 | 5/2003 |
| EP | 3046270 | 2/1982 |
| EP | 2126098 | 12/2009 |
| GB | 2370504 | 7/2002 |
| GB | 2420707 | 10/2005 |
| KR | 2013063708 | * 6/2013 |
| RU | 1808280 | * 4/1993 |
| SU | 1500244 | 8/1989 |
| WO | 200563184 | 7/2005 |
| WO | 200640596 | 4/2006 |
| WO | 2007141158 | 12/2007 |
| WO | 2009150441 | 12/2009 |
| WO | 2010147966 | 12/2010 |
| WO | 2014194260 | 12/2014 |
| WO | 2015158919 | 10/2015 |
| WO | 2015189579 | 12/2015 |

* cited by examiner

*Primary Examiner* — Alton N Pryor

(74) *Attorney, Agent, or Firm* — Bereskin & Parr LLP

(57) ABSTRACT

Herbicide compositions and methods of controlling growth of plants of the Buckthorn family (e.g. Rhamnaceae) are described herein. The herbicide compositions comprise a herbicidally effective amount of N-hydroxy-1,4-naphthalenedione or an agriculturally acceptable salt thereof, wherein N is in the range of 2-5.

9 Claims, 9 Drawing Sheets

HERBICIDE COMPOSITIONS AND METHODS FOR CONTROLLING GROWTH OF PLANTS OF THE BUCKTHORN FAMILY

TECHNICAL FIELD

The embodiments disclosed herein relate to herbicide compositions and methods for controlling the growths of plants, and specifically to herbicide compositions and methods of controlling growth of plants of the Buckthorn family.

BACKGROUND

Due to increased human invasion into previously untouched ecosystems, a host of invasive weeds has become entrenched in places where they have no natural effective competition and therefore threaten to destabilize or destroy the ecological system. One specific example of such an invasive plant is European Buckthorn (e.g. *Rhamnus cathartica*), an invasive shrub of the Buckthorn (e.g. Rhamnaceae) family that originated in Europe and has recently spread through the eastern United States and eastern Canada.

Generally, plants of the Buckthorn family are aggressive, noxious shrubs that dominate remediation and disturbed sites. Buckthorn plants are commonly aggressive seeders that shut out successions of other trees in the understory and alter the soil chemistry in places where it has dominated, thereby further impeding the ability of native species to survive.

The current forestry, restoration and agriculture practices for controlling growth of plants of the Buckthorn family require the use of mechanical techniques such as cutting and chipping trees and subsequent application of herbicides such as triclopyr or glyphosate to the cut stumps. Plants of the Buckthorn family will often re-sprout despite the direct application of these herbicides, and their seeds can remain dormant in the soil for up to 5 years.

There is therefore a need for herbicide compositions and methods for controlling growth of plants of the Buckthorn family.

SUMMARY

According to one aspect, a herbicide composition comprising a herbicidally effective amount of N-hydroxy-1,4-naphthalenedione or an agriculturally acceptable salt thereof is provided, wherein N is in the range of 2-5. The herbicide composition is for controlling growth of plants of the family Rhamnaceae.

According to another aspect of the composition, the N-hydroxy-1,4-naphthalenedione is a compound of the formula:

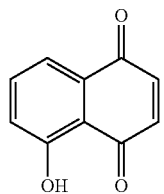 [SMILES: O=C1C=CC(=O)c2c(O)cccc21]

or an agriculturally acceptable salt thereof.

According to another aspect of the composition, the herbicidally effective amount of N-hydroxy-1,4-naphthalenedione or an agriculturally acceptable salt thereof has a concentration less than $10^{-3}$ M.

According to another aspect of the composition, the herbicidally effective amount of N-hydroxy-1,4-naphthalenedione or an agriculturally acceptable salt thereof has a concentration less than $10^{-4}$ M.

According to another aspect of the composition, the herbicidally effective amount of N-hydroxy-1,4-naphthalenedione or an agriculturally acceptable salt thereof has a concentration less than $10^{-5}$ M.

According to another aspect of the composition, the herbicidally effective amount of N-hydroxy-1,4-naphthalenedione or an agriculturally acceptable salt thereof has a concentration less than $10^{-6}$ M.

According to another aspect of the composition, the plants of the family Rhamnaceae are of the genus *Rhamnus*.

According to another aspect of the composition, the plants of the family Rhamnaceae are selected from the group of species consisting of *Rhamnus frangula* and *Rhamnus cathartica*.

According to another aspect of the composition, the herbicide composition further comprises an adjuvant.

According to another aspect, a method of controlling growth of plants of the family Rhamnaceae is provided. The method comprises the steps of: applying to plants of the family Rhamnaceae or an area adjacent the plants of the family Rhamnaceae or applying to soil or water that controls the emergence of the plants of the family Rhamnaceae a herbicidally effective amount of N-hydroxy-1,4-naphthalenedione or an agriculturally acceptable salt thereof, wherein N is in the range of 2-5.

According to another aspect of the method, the N-hydroxy-1,4-naphthalenedione is a compound of the formula:

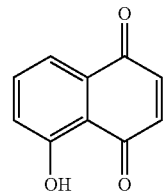 [SMILES: O=C1C=CC(=O)c2c(O)cccc21]

or an agriculturally acceptable salt thereof.

According to another aspect of the method, the herbicidally effective amount of N-hydroxy-1,4-naphthalenedione or an agriculturally acceptable salt thereof has a concentration less than $10^{-3}$ M.

According to another aspect of the method, the herbicidally effective amount of N-hydroxy-1,4-naphthalenedione or an agriculturally acceptable salt thereof has a concentration less than $10^{-4}$ M.

According to another aspect of the method, the herbicidally effective amount of N-hydroxy-1,4-naphthalenedione or an agriculturally acceptable salt thereof has a concentration less than $10^{-5}$ M.

According to another aspect of the method, the herbicidally effective amount of N-hydroxy-1,4-naphthalenedione or an agriculturally acceptable salt thereof has a concentration less than $10^{-6}$ M.

According to another aspect of the method, the plants of the family Rhamnaceae are of the genus *Rhamnus*.

According to another aspect of the method, the plants of the family Rhamnaceae are selected from the group of species consisting of *Rhamnus frangula* and *Rhamnus cathartica*.

According to another aspect of the method, the herbicide composition further comprises an adjuvant.

Additional aspects will be apparent in view of the description which follows. It should be understood however that the detailed description and the specific examples, while indicating preferred embodiments, are given by way of illustration only, since various changes and modifications will become apparent to those skilled in the art from this detailed description.

BRIEF DESCRIPTION OF THE DRAWINGS

The drawings included herewith are for illustrating various examples of articles, methods, and apparatuses of the present specification. In the drawings.

DETAILED DESCRIPTION

Figure 1:
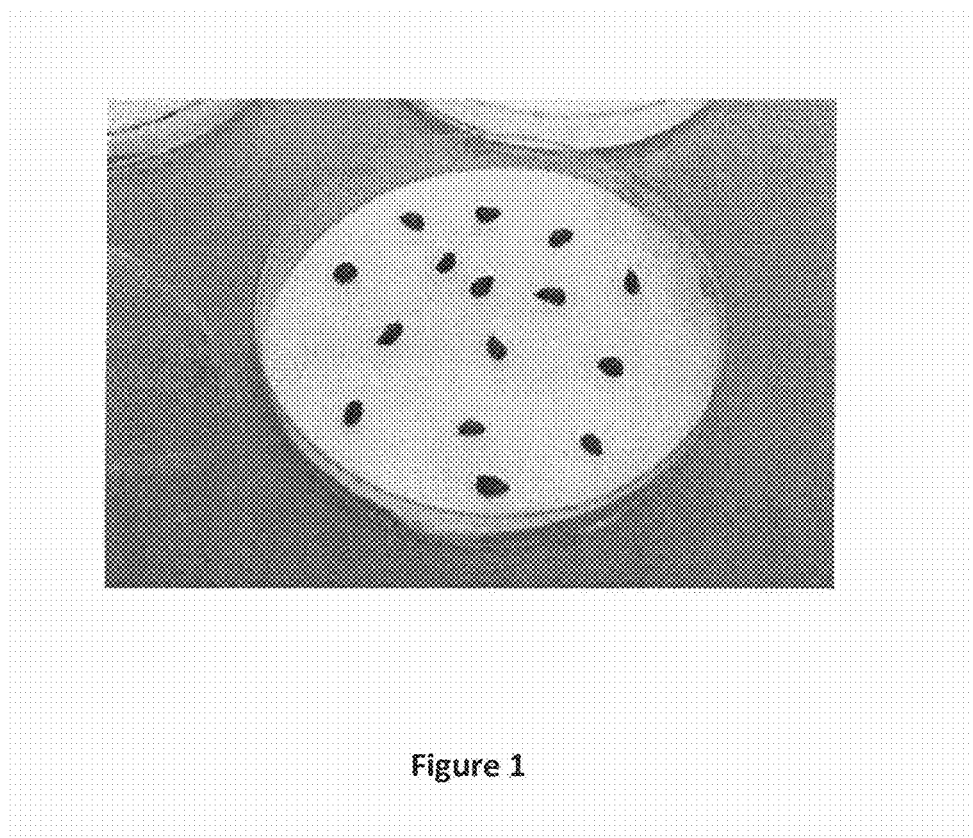
FIG. 1 is a picture of 15 Buckthorn seeds sitting on a filter paper in a Petri dish.

Various apparatus or processes will be described below to provide an example of one or more embodiments. No embodiment described below limits any claimed embodiment and any claimed embodiment may cover processes or apparatus that differ from those described below. The claimed embodiments are not limited to apparatus or processes having all of the features of any one apparatus or process described below or to features common to multiple or all of the apparatus described below. It is possible that an apparatus or process described below is not an embodiment of any claimed embodiment. Any embodiment disclosed below that is not claimed in this document may be the subject matter of another protective instrument, for example, a continuing patent application, and the applicants, inventors or owners do not intend to abandon, disclaim or dedicate to the public any such embodiment by its disclosure in this document.

The present disclosure relates to herbicidal compositions comprising a herbicidally effective amount of N-hydroxy-1,4-naphthalenedione or an agriculturally acceptable salt thereof. The present disclosure also relates to methods for controlling growth of undesirable vegetation such as but not limited to plants of the Buckthorn family.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

Compositions of the present disclosure include N-hydroxy-1,4-naphthalenedione, wherein N is in the range of 2-5. In one example, compositions of the present disclosure can include the compound of formula (I), 5-hydroxy-1,4-naphthalenedione (e.g. Juglone). Juglone occurs naturally in the leaves, roots, husks, fruit (e.g. the epicarp), and bark of plants in the Juglandaceae family, particularly the black walnut (*Juglans nigra*).

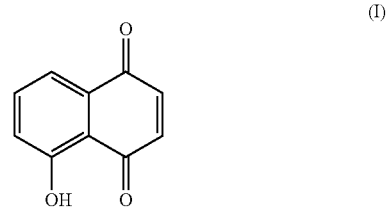 [SMILES: O=C1C=CC(=O)c2c(O)cccc21]

(I)

In some embodiments, N-hydroxy-1,4-naphthalenedione can be an agriculturally acceptable salt of N-hydroxy-1,4-naphthalenedione. Exemplary agriculturally acceptable salts of N-hydroxy-1,4-naphthalenedione can include, but are not limited to, sodium salts, potassium salts, ammonium salts or substituted ammonium salts, in particular mono-, di- and tri-C1-C8-alkylammonium salts such as methylammonium, dimethylammonium and isopropylammonium, mono-, di- and tri-hydroxy-C2-C8-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts.

Compositions of the present disclosure including N-hydroxy-1,4-naphthalenedione, or an agriculturally acceptable salt thereof, can be applied to vegetation or an area adjacent the vegetation or applied to soil or water to prevent the emergence or growth of vegetation in an amount sufficient to induce a herbicidal effect.

In some embodiments, the compositions of the present disclosure including N-hydroxy-1,4-naphthalenedione or an agriculturally acceptable salt thereof are applied to vegetation or an area adjacent the vegetation or applied to soil or water to prevent the emergence or growth of vegetation wherein the composition has a concentration of N-hydroxy-1,4-naphthalenedione less than $10^{-3}$ M.

In some embodiments, the compositions of the present disclosure including N-hydroxy-1,4-naphthalenedione or an agriculturally acceptable salt thereof are applied to vegetation or an area adjacent the vegetation or applied to soil or water to prevent the emergence or growth of vegetation wherein the composition has a concentration of N-hydroxy-1,4-naphthalenedione less than $10^{-4}$ M.

In some embodiments, the compositions of the present disclosure including N-hydroxy-1,4-naphthalenedione or an agriculturally acceptable salt thereof are applied to vegetation or an area adjacent the vegetation or applied to soil or water to prevent the emergence or growth of vegetation wherein the composition has a concentration of N-hydroxy-1,4-naphthalenedione less than $10^{-5}$ M.

In some embodiments, the compositions of the present disclosure including N-hydroxy-1,4-naphthalenedione or an agriculturally acceptable salt thereof are applied to vegetation or an area adjacent the vegetation or applied to soil or water to prevent the emergence or growth of vegetation wherein the composition has a concentration of N-hydroxy-1,4-naphthalenedione less than $10^{-6}$ M.

The compositions disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the N-hydroxy-1,4-naphthalenedione or agriculturally acceptable salt thereof.

In some embodiments, the additive includes an agriculturally acceptable adjuvant.

Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85)+ emulsifiers (15%)) or less, nonylphenol ethoxylate or less, benzylcocoalkyldimethyl quaternary ammonium salt or less, blend of petroleum hydrocarbon, alkyl esters, organic acid, and anionic surfactant or less, $C_9$-$C_{11}$ alkylpolyglycoside or less, phosphate alcohol ethoxylate or less, natural primary alcohol ($C_{12}$-$C_{16}$) ethoxylate or less, di-sec-butylphenol EO-PO block copolymer or less, polysiloxane-methyl cap or less, nonylphenol ethoxylate+urea ammonium nitrate or less, emulsified methylated seed oil or less, tridecyl alcohol (synthetic) ethoxylate (8 EO) or less, tallow amine ethoxylate (15 EO) or less, and PEG(400) dioleate-99.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and actadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophohically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48.1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

Methods of Application

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation) or post-emergence (i.e., during and/or after emergence of the undesirable vegetation including but not limited to after mechanical cutting of the vegetation (e.g. to a cut stump)).

In some embodiments, the compositions disclosed herein are applied to undesirable vegetation or an area adjacent the undesirable vegetation or applied to soil or water to prevent the emergence or growth of undesirable vegetation by spraying (e.g. foliar spraying). In some embodiments, the spraying techniques use, for example, water as a carrier.

In some embodiments, herbicidal activity is exhibited by the compositions described herein when they are applied directly to the undesirable vegetation or to the locus of the undesirable vegetation at any stage of growth or before emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of the herbicide composition applied.

The compositions and methods disclosed herein can be used for controlling undesired vegetation in non-crop areas. Exemplary non-crop areas include, but are not limited to, turfgrass, pastures, grasslands, rangelands, fallow land, rights-of-way, aquatic settings, tree and vine, wildlife management areas, or rangeland. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms.

In some embodiments, the compositions disclosed herein are used to control growth of undesired vegetation of species of the family Rhamnaceae. In certain embodiments, the species of the family Rhamnaceae is of the genus *Rhamnus*. In certain embodiments the species of the genus *Rhamnus* is selected from the group: *Rhamnus alaternus, Rhamnus alnifolia, Rhamnus arguta, Rhamnus bourgaeana, Rhamnus cathartica, Rhamnus crocea, Rhamnus davurica, Rhamnus diffusa, Rhamnus globosa, Rhamnus ilicifolia, Rhamnus japonica, Rhamnus lanceolata, Rhamnus libanotica, Rhamnus ludovici-salvatoris, Rhamnus lycioides, Rhamnus palaestina, Rhamnus pirifolia, Rhamnus prinoides, Rhamnus pumila, Rhamnus saxatilis, Rhamnus serrata, Rhamnus smithii, Rhamnus staddo, Rhamnus utilis* or is of the subgenus *Frangula* including but not limited to the species *Rhamnus befulaefolia, Rhamnus californica, Rhamnus caroliniana (Frangula caroliniana), Rhamnus frangula (Frangula alnus), Rhamnus glandulosa, Rhamnus hintonii, Rhamnus purshiana (Frangula purshiana)* and *Rhamnus rubra (Frangula rubra)*.

While the above description provides examples of one or more apparatus, methods, or systems, it will be appreciated that other apparatus, methods, or systems may be within the scope of the claims as interpreted by one of skill in the art.

By way of non-limiting illustration, examples of certain embodiments of the present disclosure are given below.

EXAMPLES

Seed Germination

Juglone was purchased from Sigma Aldrich and diluted in sterile water to a $10^{-3}$ M stock solution for 24 hours at 40° C., then further diluted to obtain $10^{-4}$, $10^{-5}$ and $10^{-6}$ M solutions. Seeds were previously collected from 3 different sites (Site 1: Iroquois Shoreline Woods Park in Oakville, Ontario, Canada, Site 2: Ignatius Jesuit Centre in Guelph, Ontario, Canada, and Site 3: Snyder Flats Conservation Area in Bloomingdale, Ontario, Canada) and then placed into cold stratification. For this experiment, seeds were removed from 40 day cold stratification and surface sterilization was done for 30 s in 3% hydrogen peroxide followed by two one minute sterile water rinses. Sheets of 90 mm filter paper were placed on the bottom of Petri plates, followed by 15 seeds, and then topped with another sheet of filter paper. A pipette then dispensed 2 ml of treatment or control onto each plate directly onto the top filter paper, thereby wetting the seeds and bottom filter paper as well. Five reps (plates) were done for each site at each treatment. Plates were then placed into Ziploc bags (to maintain humidity) and kept at 24° C. in the dark. Plates were checked every day for germination (i.e. emergence of the radicle). The number of germinated seeds per plate was recorded daily. Using Microsoft Excel, a graph was created to show the average number of germinated seeds per group with standard error. Statistics were done using JMP statistical software.

FIG. 1 shows a picture of Buckthorn seeds sitting on a filter paper in a petri dish.

All seeds that germinated did so by Day 12; no further germination was observed up to Day 32 when the experiment was ended. The overall effect on germination was analyzed for Day 12 using a Least Squares Model and a significant difference was found at different sites and at different treatments, $F_{(10,64)}=7.74$ and $p<0.001$. The significant difference between the treatments was $F_{(4,64)}=6.2$ and $p=0.003$.

It should be noted that herein, F refers to the F statistic and p refers to p value. When conducting an ANOVA test or a regression analysis to determine if the means between two populations are significantly different, the F statistic is the quotient of the dividend (variance of the group means) divided by (mean of the within group variances). The F statistic indicates if a group of variables are jointly significant. The p value is determined from the F statistic and represents the probability that the obtained results could have happened by chance. When p is $<0.05$, the result is statistically significant.

Differences between sites were also observed. Seeds from Site 3 exposed to control germinated much less than seeds from either of Site 1 or Site 2. These trends seemed to carry through to all treatments.

Figure 2:
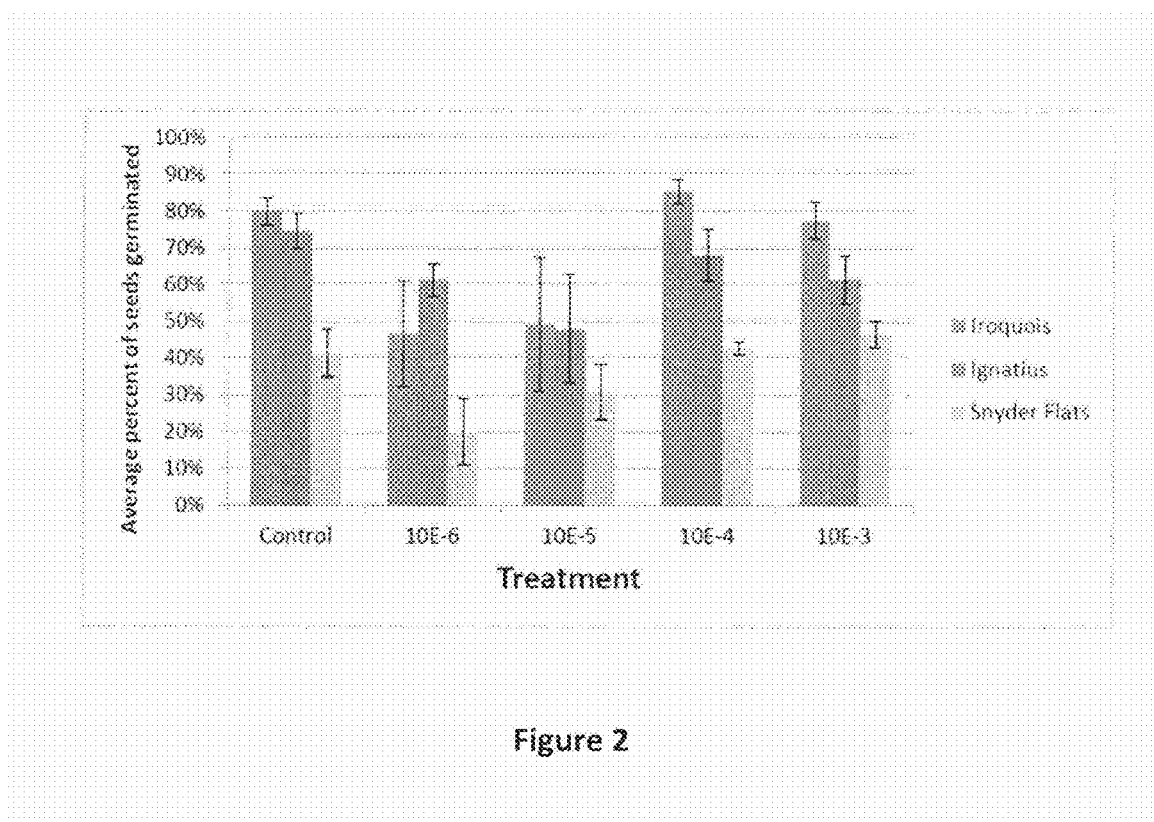
FIG. 2 is a graph showing an average percentage of Buckthorn seeds that germinated from each treatment group for each site.

FIG. 2 is a graph showing the average percentage of Buckthorn seeds that germinated from each treatment group for each site.

Individual comparisons between controls and the $10^{-6}$ M and $10^{-5}$ M dilution treatments revealed that the percentage of Buckthorn seeds that germinated was consistently significantly lower in seeds that received treatment with the concentrations of Juglone. The percentage of Buckthorn seeds that germinated appeared to increase as the concentration of Juglone increased above $10^{-5}$ M.

Figure 3:
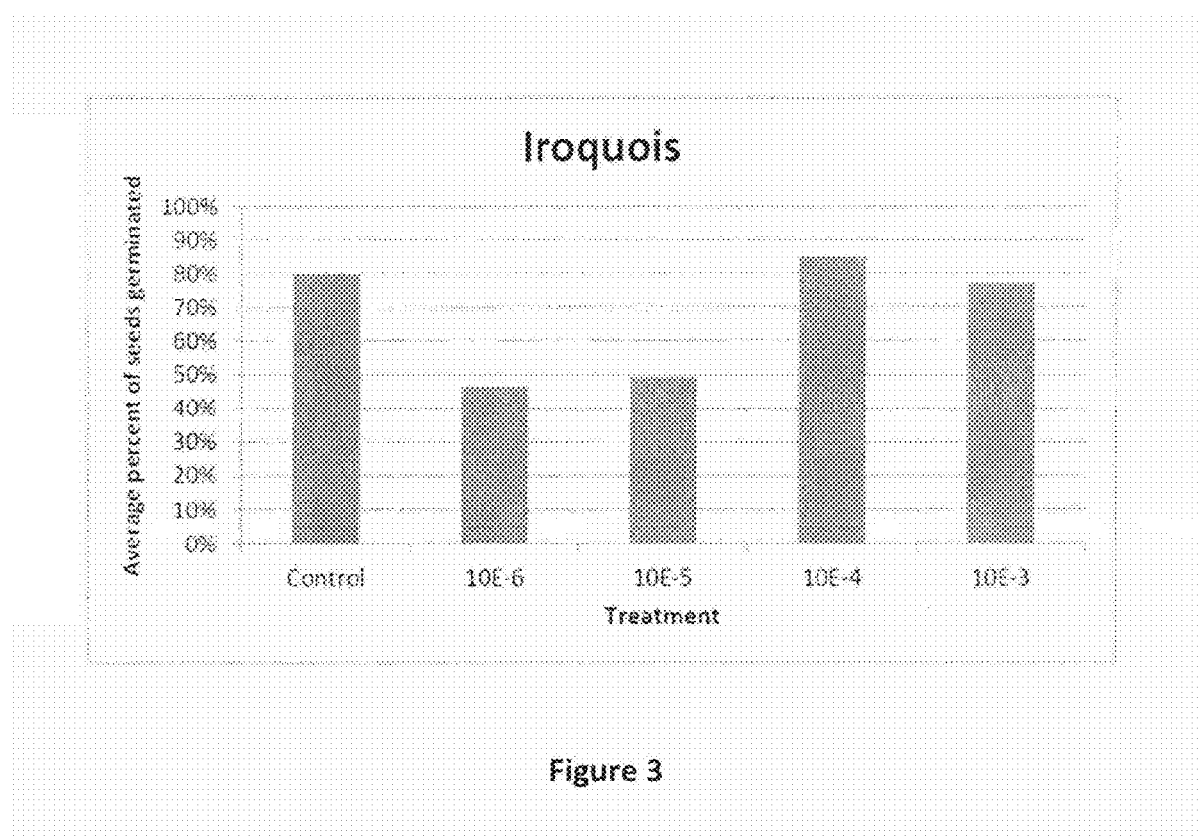
FIG. 3 is a graph showing an average percentage of Buckthorn seeds that germinated from each treatment group for seed from the Iroquois Shoreline Woods Park site in Oakville, Ontario.

FIG. 3 is a graph showing the average percentage of Buckthorn seeds that germinated from each treatment group for seeds from the Iroquois Shoreline Woods site in Oakville, Ontario (Control vs $10^{-6}$ MP: p=0.0278, one-tail T-test, Control vs $10^{-5}$ M: p=0.07, one-tail T-test).

Figure 4:
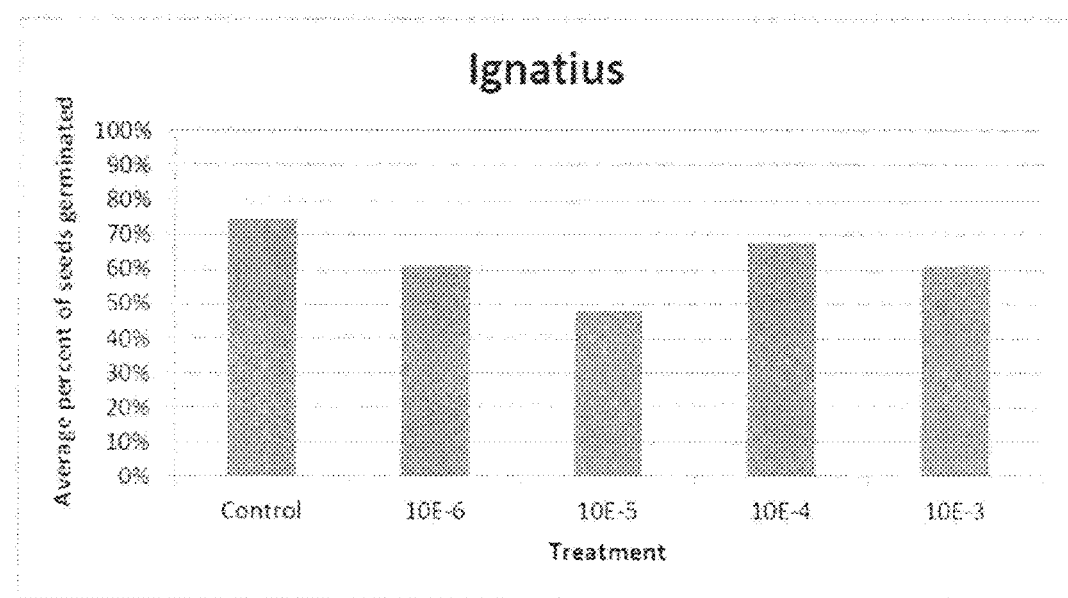
FIG. 4 is a graph showing an average percentage of Buckthorn seeds that germinated from each treatment group for seed from the Ignatius Jesuit Centre site in Guelph, Ontario.

FIG. 4 is a graph showing the average percentage of Buckthorn seeds that germinated from each treatment group for seed from the Ignatius Jesuit Centre site in Guelph, Ontario (Control vs. $10^{-6}$ M: p=0.039, one-tail T-test, Control vs $10^{-5}$ M: p=0.063, one-tail T-test).

Figure 5:
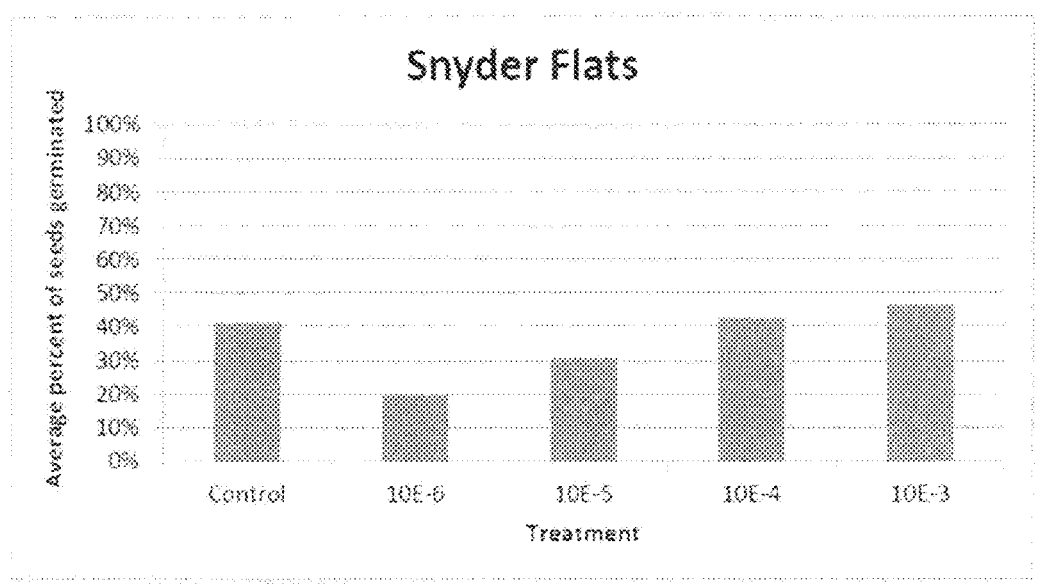
FIG. 5 is a graph showing an average percentage of Buckthorn seeds that germinated from each treatment group for seed from the Snyder Flats Conservation Area site in Bloomingdale, Ontario.

FIG. 5 is a graph showing the average percentage of Buckthorn seeds that germinated from each treatment group for seed from the Snyder Flats site (Control vs $10^{-6}$ M: p=0.045, one-tail T-test Control vs $10^{-5}$ M: p=0.1561, one-tail T-test).

The lowest concentration of Juglone ($10^{-6}$ M) was significantly effective in preventing seed germination. Differences in seed germination has also been found between sites; seeds collected from Iroquois Shoreline Woods site germinated at higher rates than those from Ignatius Jesuit Centre site, with the lowest germination seen in seeds from Snyder Flats site.

Radicle Elongation

Figure 6:
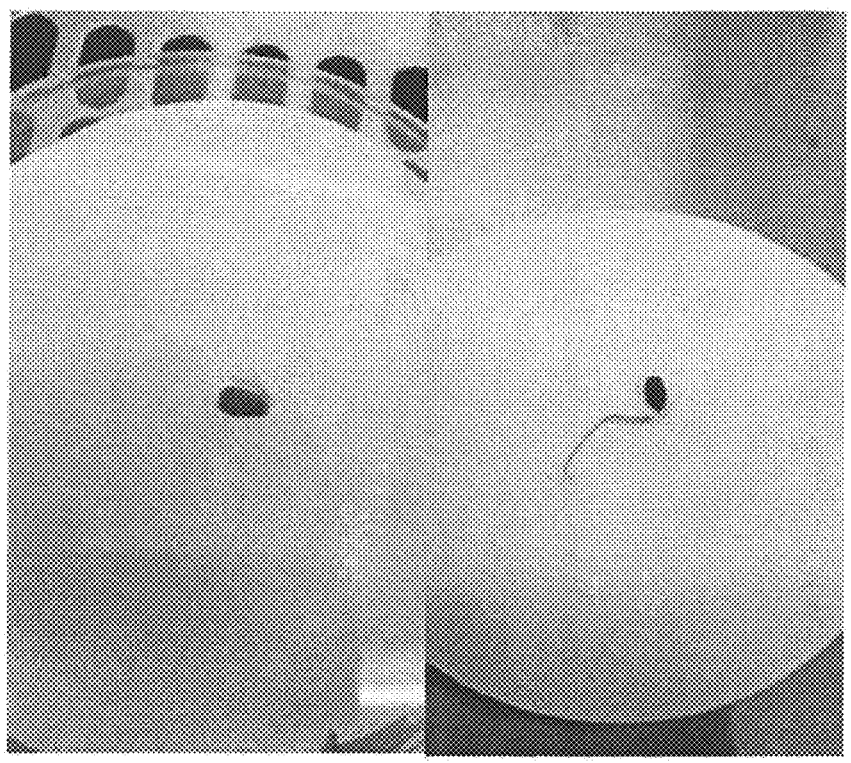
FIG. 6 is a picture of a newly emerged radicle (left) and the same radicle after seven days of elongation (right)

From the seed germination study (above), the first five (5) germinated Buckthorn seeds from each group (same treatment, same site) were set aside for radicle elongation measurements (see FIG. 6). These five were placed together in new Petri plates between two new filter papers dosed with treatment (i.e. same filter setup & treatment as germination study). For each of the 75 germinated seeds (5×15 groups), the initial length of the emerged radicle was measured. The length of the radicle was then re-measured daily for a total of 7 days. It proved to be quite difficult to accurately measure radicle length by hand (i.e. caliper) due to the delicateness of the radicle and the "curling" formations. Therefore, on Day 7 all radicles were also sacrificed and scanned on an Epson® flatbed scanner then analyzed off-label by WinRhizo™ software, which measured the full length as "Brother 1" of the inputted "root". Using Microsoft Excel, a graph was created to show the average length of radicle 7 days after emergence with standard error, when measured by hand. WinRhizo Day 7 measurements were compared to hand-measured Day 7 measurements to check for accuracy. Another graph was created to show the average growth of the radicle over time. Statistics were done using JMP™ statistical software.

FIG. 6 is a graph showing the appearance of a newly emerged radicle (left) compared to the radicle after 7 days of elongation (right).

Figure 7:
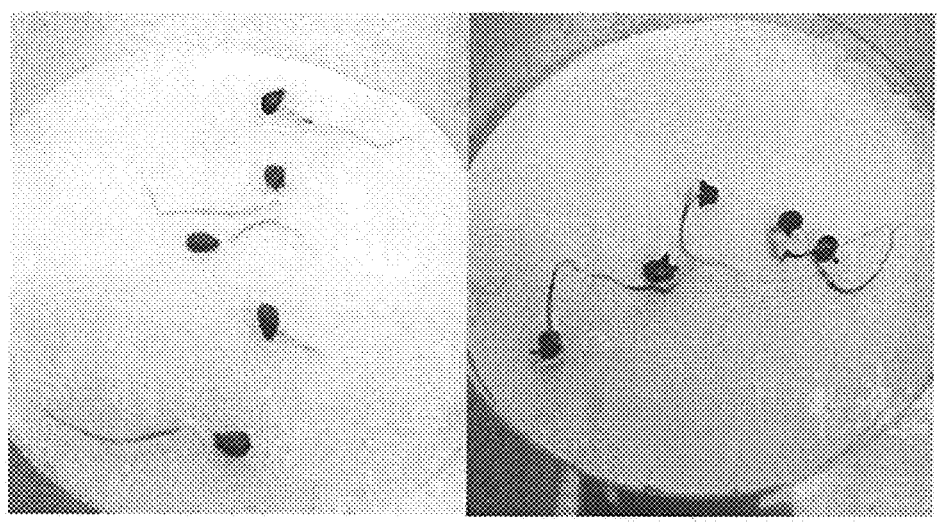
FIG. 7 is a picture showing radicles of the control (left) compared to radicles treated for seven days using a Juglone having a concentration of M (right)

An observable difference between the radicles of the control vs. the radicles exposed to the $10^{-3}$ M concentration of Juglone was indicated by a difference in colour. The control radicles were light yellow/green on Day 7 compared to the darker brown/black radicles of the $10^{-3}$ M treatment (see FIG. 7).

Growth rates on Day 7 as measured by hand were similar to those obtained by WinRhizo software; therefore, statistical analysis was carried out on the hand-measured growth data.

Figure 8A:
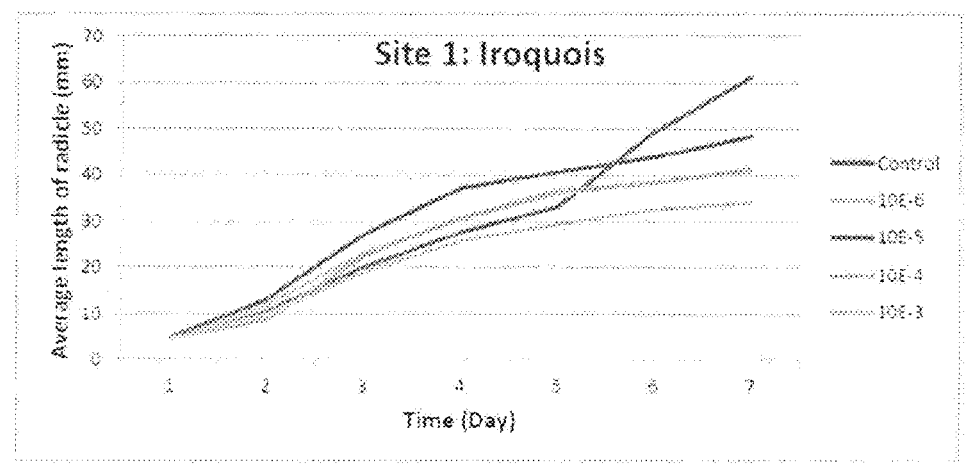
FIG. 8A is a graph showing the average length of radicles grown over seven days using seeds from the Iroquois Shoreline Woods Park site in Oakville, Ontario after treatment with various concentrations of Juglone.
Figure 8B:
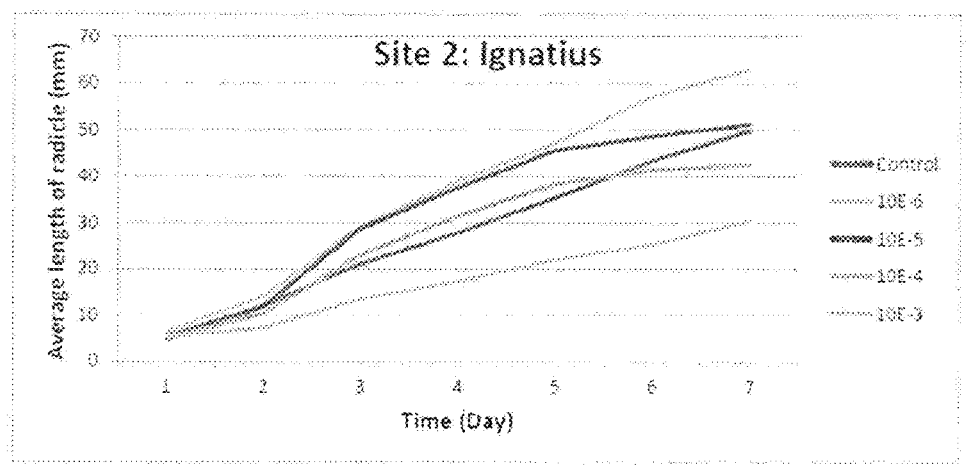
FIG. 8B is a graph showing the average length of radicles grown over seven days using seeds from the Ignatius Jesuit Centre site in Guelph, Ontario after treatment with various concentrations of Juglone.
Figure 8C:
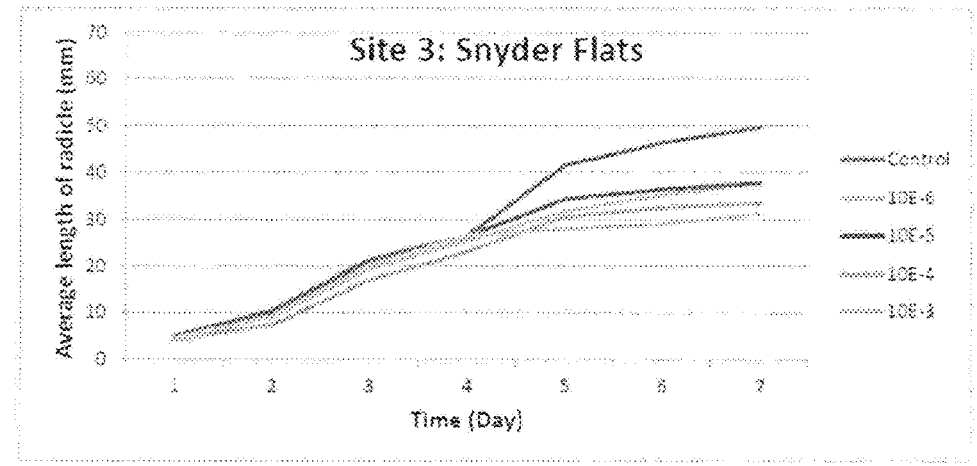
FIG. 8C is a graph showing the average length of radicles grown over seven days using seeds from the Snyder Flats Conservation Area site in Bloomingdale, Ontario after treatment with various concentrations of Juglone.

The growth rates of seed radicles were analyzed using a multivariate analysis of variance (MANOVA, repeated measures). There was no significant difference ($F_{(4,20)}$=0.38 and p=0.1485) in radicle growth between treatments of various concentrations of Juglone for seed radicles germinated from seeds from the Iroquois Shoreline Woods Park site in Oakville, Ontario (see FIG. 8A). However, there was a significant difference ($F_{(4,19)}$=0.73 and p=0.0264) in radicle growth between treatments of various concentrations of Juglone for seed radicles germinated from seeds from the Ignatius Jesuit Centre site, in Guelph, Ontario and more specifically, it was found that concentrations of $10^{-3}$ M of Juglone limited radicle elongation significantly. There was no significant difference ($F_{(4,19)}$=0.17 and p=0.5339) in radicle growth between treatments of various concentrations of Juglone for seed radicles germinated from seeds from the Snyder Flats Conservation Area site in Bloomingdale, Ontario (see FIG. 8C).

Figure 9:
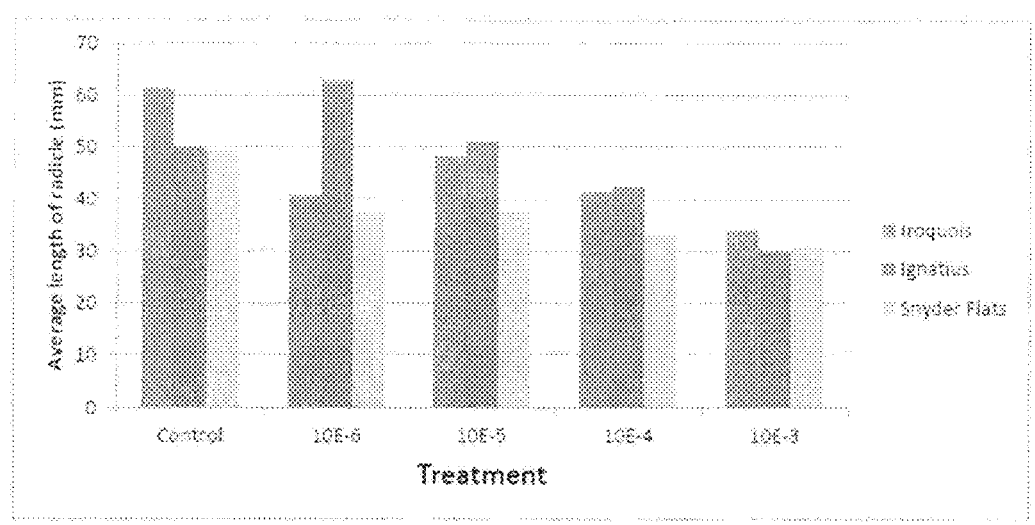
FIG. 9 is a graph showing a comparison of effects radicle growth of Buckthorn seeds collected from the three aforementioned sites in southern Ontario after treatment with various concentrations of Juglone.

When the treatment effects (net WinRhizo values) were compared by ANOVA (2-way with replication), significant difference in growth (p=0.0005) was detected among the treatments. T-tests comparing controls and Juglone treatments detected significantly reduced growth of radicles growing in the presence of Juglone concentrations of $10^{-3}$ M for all sites, but at only for the Iroquois Shoreline Woods Park site and Snyder Flats Conservation Area site for concentrations of $10^{-4}$ M. Growth reduction was not achieved on seed from any site with more dilute concentrations (see FIG. 9).

A concentration of $10^{-3}$ M Juglone significantly reduced radicle elongation over seven days, compared to controls, from seed from all three sites. Radicle growth from seed from two sites, the Iroquois Shoreline Woods Park site and Snyder Flats Conservation Area site, was also reduced significantly by Juglone at a concentration of $10^{-4}$ M.

The growth curves appeared to be continuing to diverge after seven days. In addition, the blackening of treated radicles suggests a possible damaging effect by the Juglone.

While the above description provides examples of one or more apparatus, methods, or systems, it will be appreciated that other apparatus, methods, or systems may be within the scope of the claims as interpreted by one of skill in the art.

What is claimed is:

1. A method of controlling growth of plants of the family Rhamnaceae comprising the steps of:
   applying to the plants of the family Rhamnaceae or an area adjacent plants of the family Rhamnaceae or applying to soil or water where the plants are expected to emerge a herbicidally effective amount of N-hydroxy-1,4-naphthalenedione or an agriculturally acceptable salt thereof, wherein N is in the range of 2-5.

2. The method of claim 1, wherein the N-hydroxy-1,4-naphthalenedione is a compound of the formula:

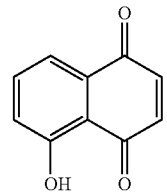 [SMILES: O=C1C=CC(=O)c2c(O)cccc21]

or an agriculturally acceptable salt thereof.

3. The method of claim 1, wherein the herbicidally effective amount of N-hydroxy-1,4-naphthalenedione or an agriculturally acceptable salt thereof has a concentration less than $10^{-3}$ M.

4. The method of claim 3, wherein the herbicidally effective amount of N-hydroxy-1,4-naphthalenedione or an agriculturally acceptable salt thereof has a concentration less than $10^{-4}$ M.

5. The method of claim 4, wherein the herbicidally effective amount of N-hydroxy-1,4-naphthalenedione or an agriculturally acceptable salt thereof has a concentration less than $10^{-5}$ M.

6. The method of claim 5, wherein the herbicidally effective amount of N-hydroxy-1,4-naphthalenedione or an agriculturally acceptable salt thereof has a concentration less than $10^{-6}$ M.

7. The method of claim 1, wherein the plants of the family Rhamnaceae are of the genus *Rhamnus*.

8. The method of claim 1, wherein the plants of the family Rhamnaceae are selected from the group of species consisting of *Rhamnus frangula* and *Rhamnus cathartica*.

9. The method of claim 1, wherein the N-hydroxy-1,4-naphthalenedione is combined with an adjuvant.

* * * * *